United States Patent
Zhang et al.

(10) Patent No.: US 10,029,960 B2
(45) Date of Patent: Jul. 24, 2018

(54) CATALYSTS AND METHODS FOR PRODUCING PROPYLENE FROM ETHYLENE AND BUTENE

(71) Applicant: Lyondell Chemical Technology, L.P., Houston, TX (US)

(72) Inventors: Lei Zhang, Houston, TX (US); Daniel F. White, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 15/414,384

(22) Filed: Jan. 24, 2017

(65) Prior Publication Data

US 2017/0217856 A1 Aug. 3, 2017

Related U.S. Application Data

(60) Provisional application No. 62/288,954, filed on Jan. 29, 2016.

(51) Int. Cl.
| | | |
|---|---|---|
| *C07C 6/04* | (2006.01) | |
| *C07C 5/25* | (2006.01) | |
| *B01J 21/10* | (2006.01) | |
| *B01J 23/30* | (2006.01) | |

(52) U.S. Cl.
CPC ............ C07C 6/04 (2013.01); B01J 21/10 (2013.01); B01J 23/30 (2013.01); C07C 5/2512 (2013.01); *C07C 2521/08* (2013.01); *C07C 2521/10* (2013.01); *C07C 2523/30* (2013.01)

(58) Field of Classification Search
CPC ......... C07C 5/2512; C07C 6/04; C07C 11/06; C07C 11/08; C07C 2521/08; C07C 2521/10; C07C 2523/30; B01J 21/10; B01J 23/30
See application file for complete search history.

(56) References Cited

U.S. PATENT DOCUMENTS

| | | | |
|---|---|---|---|
| 4,684,760 A | | 8/1987 | Drake |
| 5,043,520 A | * | 8/1991 | Hamilton, Jr. ........... B01J 29/69 585/646 |
| 9,023,753 B2 | * | 5/2015 | Ramachandran ...... B01J 23/007 502/176 |
| 2004/0267067 A1 | | 12/2004 | Bridges et al. |
| 2005/0250969 A1 | | 11/2005 | Bridges |
| 2008/0312481 A1 | | 12/2008 | Leyshon |
| 2009/0281364 A1 | | 11/2009 | Halsey |
| 2011/0152595 A1 | | 6/2011 | Takai et al. |
| 2012/0016172 A1 | | 1/2012 | Miyazoe et al. |
| 2016/0229769 A1 | | 8/2016 | Ernst et al. |
| 2016/0347687 A1 | | 12/2016 | Stoyanova et al. |

FOREIGN PATENT DOCUMENTS

| | | |
|---|---|---|
| EP | 234498 A2 | 9/1987 |
| EP | 2330091 A1 | 6/2011 |
| EP | 2415739 A1 | 2/2012 |
| EP | 2848300 A1 | 3/2015 |
| EP | 2891643 A1 | 7/2015 |
| WO | WO-20080153643 A1 | 12/2008 |

OTHER PUBLICATIONS

The International Search Report and Written Opinion for PCT/US2017/014749 dated Apr. 5, 2017.

* cited by examiner

*Primary Examiner* — Sharon Pregler

(57) ABSTRACT

The present disclosure relates to chemical catalysts and methods that may be used for the production and/or inter-conversion of olefins. In some embodiments, methods for producing propylene from ethylene and butene comprising, (a) obtaining a catalyst composition comprising an isomerization catalyst and a disproportionation catalyst, wherein the weight ratio of the isomerization catalyst to the disproportionation catalyst is from 10:1 to 1:10; and (b) reacting butene with ethylene at a temperature from about 500° F. (260° C.) to about 650° F. (350° C.) in the presence of the catalyst composition under conditions sufficient to produce propylene are provided.

12 Claims, 9 Drawing Sheets

CATALYSTS AND METHODS FOR PRODUCING PROPYLENE FROM ETHYLENE AND BUTENE

CROSS-REFERENCE TO RELATED APPLICATIONS

This application claims the benefit of priority to U.S. Provisional Application No. 62/288,954, filed on Jan. 29, 2016, which is incorporated herein by reference in its entirety.

FIELD OF THE INVENTION

The present disclosure relates to chemical catalysts and methods that may be used for the production and/or interconversion of olefins.

BACKGROUND OF THE INVENTION

Propylene (propene) is a commercially important olefin product and a byproduct of oil refining and natural gas processing. Propylene is also produced by on-purpose production methods, such as butene isomerization combined with olefin metathesis chemistry (see, for example, FIG. 1). Olefin metatheses, which are also known as disproportionation, are reversible reactions in which double bonds of, for example, ethylene and 2-butene (B2) are broken and then reformed as propylene. $WO_3$ supported on $SiO_2$ is one type of disproportionation catalyst that has been used, and MgO is one type of isomerization catalyst that has been used. The chemistry involves many side reactions in the disproportionation (DP) reactors (FIG. 2), including, e.g., the half productive route for propylene via butene (B) self-metathesis and undesirable consumption of product propylene with 1-butene (B1) to produce higher olefins ($C_{5+}$ olefins) and ethylene. Current methods are energy intensive, relying on high heat (e.g., 650° F.), and significant quantities of isomerization catalyst, i.e. a high weight ratio of isomerization catalyst to the disproportionation catalyst (see, e.g., FIG. 3).

SUMMARY OF THE INVENTION

In one aspect, the present disclosure provides methods comprising:
(a) obtaining a catalyst composition comprising an isomerization catalyst and a disproportionation catalyst, wherein the weight ratio of the isomerization catalyst to the disproportionation catalyst is from 10:1 to 1:10; and
(b) reacting butene with ethylene at a temperature from about 500° F. (260° C.) to about 650° F. (350° C.) in the presence of the catalyst composition under conditions sufficient to produce propylene.

In some embodiments, the ethylene and the butene are reacted at a temperature from about 500° F. (260° C.) to about 550° F. (288° C.).

In some embodiments, the weight ratio of the isomerization catalyst to the disproportionation catalyst is from about 4:1 to about 1:4. In some of these embodiments, the weight ratio of the isomerization catalyst to the disproportionation catalyst is about 1:1.

In some embodiments, the isomerization catalyst is a zeolite, alumina, or a basic metal oxide selected from the group consisting of an alkali metal oxide, an alkaline earth metal oxide, and a rare earth metal oxide. In some of these embodiments, the isomerization catalyst is MgO.

In some embodiments, the disproportionation catalyst comprises:
(a) a transition metal oxide; and
(b) a solid support;
wherein the transition metal oxide is deposited on the solid support.

In some embodiments, the transition metal oxide is an oxide of molybdenum, tungsten, cobalt, ruthenium, rhenium, or a mixture of two or more of these. For example, in some embodiments, the transition metal oxide is $WO_3$.

In some embodiments, the solid support is alumina or silica.

In some embodiments, the ethylene and the butene are reacted at a pressure from about 5 psig (0.14 MPa) to about 600 psig (4.24 MPa).

In some embodiments, the mole ratio of ethylene to butene is from about 0.5:1 to about 5:1.

In some embodiments, the weight hourly space velocity of the reaction is from about 1 $hr^{-1}$ to 100 $hr^{-1}$.

In some embodiments, the method results in:
(a) a butene conversion percentage of greater than 55% relative to the amount of butene;
(b) a propylene selectivity percentage of greater than 85% relative to the total reaction products; or
(c) a propylene yield of greater than 50% based on the amount of butene.

In another aspect, the present disclosure provides methods comprising:
(a) obtaining a catalyst composition comprising an isomerization catalyst and a disproportionation catalyst, wherein the weight ratio of the isomerization catalyst to the disproportionation catalyst is from 10:1 to 1:10; and
(b) reacting butene with ethylene at a temperature from about 500° F. (260° C.) to about 600° F. (316° C.) in the presence of the catalyst composition under conditions sufficient to produce an $alkene_{(C5+)}$.

In some embodiments, the disproportionation catalyst is a transition metal oxide on a solid support, and wherein the amount of transition metal oxide is from about 1 wt. % to about 30 wt. % of the disproportionation catalyst.

In some embodiments, the solid support is alumina or silica.

In some embodiments, the reaction is carried out in a continuous reactor.

In some embodiments, the $alkene_{(C5+)}$ is a mixture of five-carbon and/or more alkenes including pentene isomers. In some embodiments, the $alkene_{(C5+)}$ comprises 2-pentene and/or 3-hexene.

In another aspect, the present disclosure provides methods comprising:
(a) obtaining a catalyst composition wherein the catalyst composition is an isomerization catalyst and a disproportionation catalyst and the weight ratio of the isomerization catalyst and a disproportionation catalyst is 10:1 to 1:10; and
(b) reacting $alkene_{(C2-12)}$ with ethylene, propylene, or butene at a temperature from about 500° F. (260° C.) to about 600° F. (316° C.) in the presence of the catalyst composition to produce an $alkene_{(C2-8)}$.

While multiple embodiments are disclosed, still other embodiments will become apparent to those skilled in the art from the following detailed description. As will be apparent, certain embodiments, as disclosed herein, are capable of modifications in various aspects, without departing from the spirit and scope of the claims as presented herein. Accordingly, the drawings and detailed description are to be regarded as illustrative in nature and not restrictive.

BRIEF DESCRIPTION OF THE DRAWINGS

The following figures illustrate various embodiments of the subject matter disclosed herein. The claimed subject matter may be understood by referring to the following description taken in conjunction with the accompanying figures, in which like reference numerals identify like elements, and in which:

DETAILED DESCRIPTION OF THE INVENTION

Figure 1:
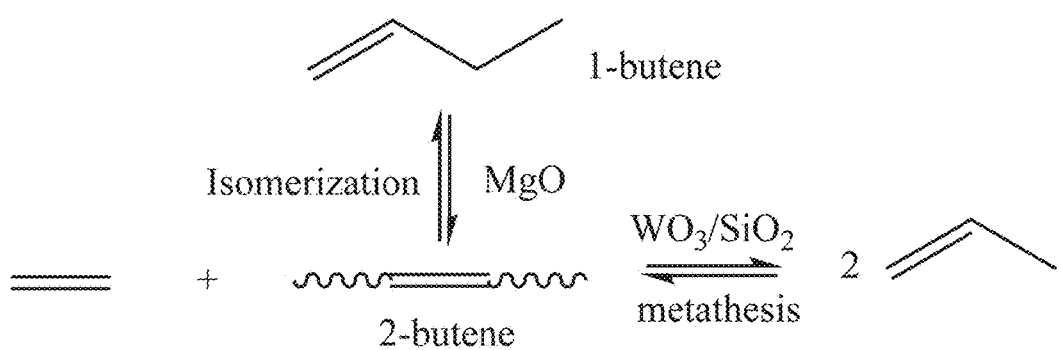
FIG. 1 shows a simplified schematic overview of an example of on-purpose production of propylene from ethylene and butenes (2-butene includes both trans- and cis-2-butene).
Figure 2:
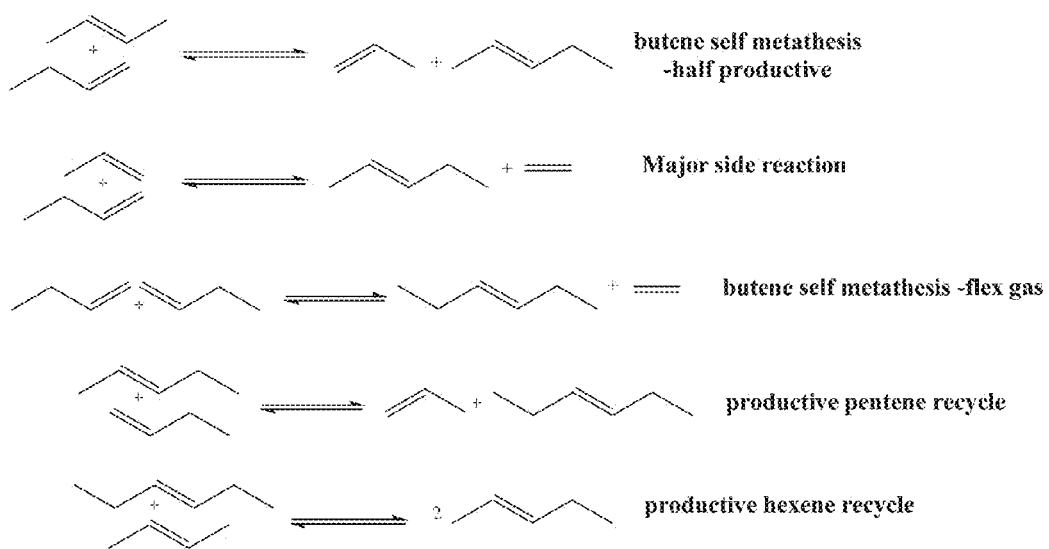
FIG. 2 shows potential side reactions that may occur in a disproportionation reactor. While trans-2-butene is depicted therein, cis-2-butene generally reacts in a similar manner.

In one aspect, the present disclosure provides methods of making propylene comprising:
(a) obtaining a catalyst composition comprising an isomerization catalyst and a disproportionation catalyst, wherein the weight ratio of the isomerization catalyst to the disproportionation catalyst is from 10:1 to 1:10; and
(b) reacting butene with ethylene at a temperature from about 500° F. (260° C.) to about 650° F. (350° C.) in the presence of the catalyst composition under conditions sufficient to produce propylene.

In another aspect, the present disclosure provides methods of making propylene comprising:
(a) obtaining a catalyst composition comprising an isomerization catalyst and a disproportionation catalyst, wherein the weight ratio of the isomerization catalyst to the disproportionation catalyst is from 10:1 to 1:10; and
(b) reacting butene with ethylene at a temperature from about 500° F. (260° C.) to about 600° F. (316° C.) in the presence of the catalyst composition under conditions sufficient to produce an alkene$_{(C5+)}$.

In another aspect, the present disclosure provides methods of making propylene comprising:
(a) obtaining a catalyst composition wherein the catalyst composition is an isomerization catalyst and a disproportionation catalyst and the weight ratio of the isomerization catalyst and a disproportionation catalyst is 10:1 to 1:10; and
(b) reacting alkene$_{(C2-12)}$ with ethylene, propylene, or butene at a temperature from about 500° F. (260° C.) to about 600° F. (316° C.) in the presence of the catalyst composition to produce an alkene$_{(C2-8)}$.

In some embodiments, these methods may be used to make more propylene at higher selectivity due to increased 2-butene concentration.

I. Disproportionation Catalysts

In some embodiments, the disproportionation catalyst comprises:
(a) a transition metal oxide; and
(b) a solid support;
wherein the transition metal oxide is deposited on the solid support. In some embodiments, the solid support is alumina, silica, zeolite, clay, zirconia, titania and/or combinations thereof. In some embodiments, the solid support is a mixture of one or more of these.

In some embodiments, the transition metal oxide is an oxide of molybdenum, tungsten, cobalt, ruthenium, rhenium, or a mixture of two or more of these. For example, in some embodiments, the transition metal oxide is $WO_3$.

In some embodiments, the disproportionation catalyst is a transition metal oxide on a solid support, and wherein the amount of transition metal oxide is from about 1 wt. % to about 30 wt. % of the disproportionation catalyst. In some of these embodiments, the amount is from about 5 wt. % to about 20 wt. %. In some of these embodiments, the amount is from about 4 wt. % to about 12 wt. %. In some of these embodiments, the amount is from about 7 wt. % to about 8 wt. %. In some embodiments, the solid support is alumina or silica.

In some embodiments, the disproportionation catalyst is formulated and/or processed (together with or separately from the isomerization catalyst) as a fixed bed, as pellets, granules, beads, extrudates, tablets, agglomerates, or as a honeycomb monolith.

II. Isomerization Catalysts

In some embodiments, the isomerization catalyst is a zeolite, alumina, or a basic metal oxide selected from the group consisting of an alkali metal oxide, an alkaline earth metal oxide, and a rare earth metal oxide. In some of these embodiments, the isomerization catalyst is MgO. In other of these embodiments, the isomerization catalyst is CaO, BeO, SrO, BaO, other metal oxides and/or combinations thereof. In other embodiments, the isomerization catalyst is an alumina such as $Al_2O_3$ or other zeolite material.

In some embodiments, the isomerization catalyst has a surface area greater than 1 $m^2/g$. In some of these embodiments, the surface area is greater than about 5 $m^2/g$.

In some embodiments, the isomerization catalyst is activated under inert atmosphere, for example argon or nitrogen. In some of these embodiments, the activation is conducted at a temperature from about 450° F. (232.2° C.) to about 1,500° F. to (815.6° C.). In some of these embodiments, the activation is conducted at a temperature from about 600° F. (315.6° C.) to about 1,200° F. to (648.9° C.). In some embodiments the activation is conducted for a time interval from 0.5 hours to 30 hours. In some embodiments, the isomerization catalyst is regenerated using oxygen, for example, to burn off any deposited carbonaceous cokes.

In some embodiments, the disproportionation catalyst is formulated and/or processed (together with or separately from the isomerization catalyst) as a fixed bed, as pellets, granules, beads, extrudates, tablets, agglomerates, or as a honeycomb monolith.

III. Reaction Conditions

General reaction conditions that may be used for disproportionations and isomerizations are provided by U.S. Pat. Nos. 6,683,019 and 8,586,813, which are incorporated herein by reference. In some embodiments, the reactions are carried out in a gas-phase process. In some embodiments, the reactions are carried out in a continuous process.

In some embodiments, the weight ratio of the disproportionation catalyst to the isomerization catalyst is from about 10:1 to about 1:10. In some embodiments, the weight ratio of the disproportionation catalyst to the isomerization catalyst is from about 4:1 to about 1:4. In some embodiments, the weight ratio of the disproportionation catalyst to the isomerization catalyst is from about 3:1 to about 1:1. In some embodiments, the weight ratio of the disproportionation catalyst to the isomerization catalyst is from about 1:1 to about 1:3. In some of these embodiments, the weight ratio of the disproportionation catalyst to the isomerization catalyst is about 1:1.

In some embodiments, the ethylene and the butene are reacted at a temperature in a range of from about 500° F. (260° C.) to about 650° F. (350° C.) in the presence of the catalyst composition under conditions sufficient to produce propylene. In some embodiments, the ethylene and the butene are reacted at a temperature from about 500° F. (260° C.) to about 600° F. (316° C.). In some embodiments, the ethylene and the butene are reacted at a temperature from about 500° F. (260° C.) to less than 600° F. (316° C.). In some embodiments, the ethylene and the butene are reacted at a temperature from about 500° F. (260° C.) to about 550° F. (288° C.). In some embodiments, the ethylene and the butene are reacted at a temperature of about 527° F. (275° C.).

In some embodiments, the ethylene and the butene are reacted at a pressure from about 1 psig (0.11 MPa) to about 1,500 psig (10.4 MPa). In some embodiments, the ethylene and the butene are reacted at a pressure from about 5 psig (0.14 MPa) to about 600 psig (4.24 MPa). In some embodiments, the ethylene and the butene are reacted at a pressure from about 450 psig (3.20 MPa).

In some embodiments, the mole ratio of ethylene to butene is from about 0.5:1 to about 5:1.

In some embodiments, the weight hourly space velocity of the reaction is from about 0.01 hr$^{-1}$ to 1,000 hr$^{-1}$. In some embodiments, the weight hourly space velocity of the reaction is from about 1 hr$^{-1}$ to 100 hr$^{-1}$. In some embodiments, the weight hourly space velocity of the reaction is from about 5 hr$^{-1}$ to 50 hr$^{-1}$.

In some embodiments, the present technology produces a butene conversion percentage of greater than 55% relative to the amount of butene. For example, in some embodiments, the methods described herein result in a butene conversion percentage of 60-85% relative to the amount of butene.

In some embodiments, the present technology produces a propylene selectivity percentage of greater than 85% relative to the total reaction products. For example, in some embodiments, the method results in a propylene selectivity percentage of greater than 89% or greater than 93% relative to the total reaction products.

In some embodiments, the present technology produces a propylene yield of greater than 50% based on the total amount of olefin feeds. In some embodiments, these methods may be used to make more propylene at higher selectivity due to increased 2-butene concentration.

In some embodiments, higher propylene selectivity is favored at lower temperature. In some embodiments, these methods produce ultra-pure polymer grade propylene. In some embodiments, the product ratios depends on the feed type, B1 only, or B2 only, or mixtures having different B1 and B2 ratios.

In some embodiments, the alkene$_{(C5+)}$ is a mixture of pentenes. In some embodiments, the mixture comprises 2-pentene and/or 3-hexene and additional five-carbon or more alkenes.

IV. Process Scale-Up

The above methods can be further modified and optimized for preparative, pilot- or large-scale production, either batch or continuous, using the principles and techniques of process chemistry as applied by a person skilled in the art. Such principles and techniques are taught, for example, in *Practical Process Research & Development* (2012).

V. Definitions

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the variation of error for the device, the method being employed to determine the value, or the variation that exists among the studies.

The term "alkyl" when used in the context of this application is an aliphatic, straight or branched chain consisting of carbon and hydrogen atoms consistent with standard IUPAC nomenclature. When the term is used in conjunction with the term "substituted", one or more of the hydrogen atoms of the alkyl group has been replaced with —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

"B" refers to total butene (all isomers). "B1" refers to 1-butene. "B2" refers to 2-butene, including cis-2-butene and trans-2-butene.

"C$_2$$^=$", C2 and E are used interchangeably to refer to ethylene.

C$_3$$^=$ is used to refer to propylene.

"C$_4$$^=$", C4 and B are used interchangeably to refer to butene.

The term "dimer butene" refers to butene made from ethylene dimerization process.

The term "butene conversion" or "C4 conversion" when used in the context of this application means the amount of butene converted into product. In some aspects, the formula:

$$C4 \text{ conversion (wt. or mol \%)} = 1 - \frac{GC\ C4\ (\text{wt. \%})}{C4\ \text{feed (wt. \%)}}$$

is used to calculate the butene conversion.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The abbreviation "exp." or "Exp." refers to experiment.

A "method" is series of one or more steps undertaking lead to a final product, result or outcome. As used herein, the word "method" is used interchangeably with the word "process".

The term "alkene" as used in this application refers to an aliphatic group which contains at least one carbon carbon double bond and is defined according to the IUPAC nomenclature standards. Some non-limiting examples of olefins include styrene, ethylene, propylene, butene, pentene, hexene, heptene, octene, nonene, decene and dodecene. In some aspects, the olefin has been substituted such that one or more of the hydrogen atoms of the olefin has been replaced with —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —$N(CH_3)_2$, —C(O)$NH_2$, —OC(O)$CH_3$, and/or —S(O)$_2NH_2$.

The term "psig" is a measurement of the pressure in pounds per square inch relative to atmospheric pressure. The values given in pascals (Pa) are relative to vacuum.

The term "propylene selectivity" or "C3 selectivity" when used in the context of this application means the amount of propylene produced relative to the amount of by-products produced. In some aspects, the formula:

$$C3 \text{ selectivity (wt \%)} = \frac{GC\ C3\ (wt.\ \%)}{\sum GC\ C3, 5, 6, 7, 8\ \text{olefins (wt \%)}}$$

is used to calculate the propylene selectivity.

The term "propylene yield" or "C3 yield" when used in the context of this application means the amount of propylene produced relative to the amount of starting material. In some aspects, the formula:

$$C3 \text{ yield (wt \%)} = \frac{GC\ C3\ (wt.\ \%)}{\sum GC\ C2\text{-}8\ \text{olefins (wt \%)}}$$

is used to calculate the propylene yield.

"SLPH" refers to "standard liter per hour".

The term "transition metal" is used to describe a metal atom, ion or salt comprising the transition metal selected from elements in columns 3-12 on the periodic table. The transition metals that may be used herein include elements from columns 6-9 on the period table. In some embodiments, the transition metal is tungsten, cobalt, molybdenum, ruthenium, or rhenium. Furthermore, the term "alkali metal" or "group 1 metal" is used to describe a metal atom, ion or salt comprising the alkali metal selected from the elements in column 1 on the periodic table. The term "alkali metal" or "Group 1 metal" may be used to describe a metal atom or ion selected from lithium, sodium, potassium, rubidium, or cesium. In some embodiments, the term is used to describe a metal atom or ion selected from lithium, sodium, or potassium.

The term "weight hourly space velocity" or "weight hourly space volume" is a measure of the amount of reactant that can be processed during a given unit time. The term is used to describe the mass of the reactant being fed into the reactor per mass of catalyst present in the reactor.

The abbreviations "wt. %," "wt. %" and "wt %" synonymously correspond to weight percentage.

The above definitions supersede any conflicting definition in any reference that is incorporated by reference herein. The fact that certain terms are defined, however, should not be considered as indicative that any term that is undefined is indefinite. Rather, the terms used are believed to describe the appended claims in terms such that one of ordinary skill can appreciate.

EXAMPLES

The following examples are included to demonstrate embodiments of the appended claims. Those of skill in the art should appreciate that many changes can be made in the specific embodiments which are disclosed and still obtain a like or similar result without departing from the spirit and scope of the disclosure herein.

Example 1: Methods and Materials i. Materials

All experiments were performed at lab scale fixed bed reactors with 13 mL catalyst. Feeds were purchased from Praxair, including ethylene, liquid butenes, helium and argon. Ethylene (ultra-high purity, 99.999%) and liquid butene (C.P grade) were each purified through a set of guard beds including R3-11G (BASF) for oxygen removal and 3A molecular sieve for moisture. Helium (6.0 research grade) was used to pressurize the butene feed. As the process flow was downward, both ethylene and butene feeds at room temperature were mixed right above the reactor after their individual flow meters and heated through the top of reactor by silicon carbide filler before entering the layer of catalyst bed. The catalysts for the study were 3-5 mm white tablet of pure MgO for olefin isomerization and 12+ mesh granular $WO_3$ (5-9 wt % of W) supported on $SiO_2$ ($WO_3/SiO_2$) for olefin metathesis.

Upon grinding and sieving (13-18 mesh), about 13.2 mL of catalysts were loaded in reactors and activated under Argon (99.999%, 5.0 grade) for 18 hrs at 475° C. before processing any hydrocarbon. Half way inside the catalyst bed was a thermal couple for reaction temperature reading. A typical process condition included 450 psig, ethylene flow rate of 15.9 SLPH and butene of 33 gram/h and a temperature ranging from 200 to 350° C. The reaction effluent was analyzed via an online GC-FID analyzer for $C_1$-$C_8$ hydrocarbon determination using effect carbon number method. The tubing between the reactor outlet and GC was heat-traced at 75° C. during operation to prevent potential accumulation hydrocarbon liquids. Excess of effluent was sent to the site thermal oxidizer.

ii. Calculations

Outputs for the process evaluation include C3 yield, C3 selectivity, and butene conversion ("C4 conversion"). The calculations used to determine the catalyst performance and reaction results are presented below.

$$C3 \text{ yield (wt. \%)} = \frac{GC\ C3\ (wt.\ \%)}{\sum GC\ C2\text{-}8\ \text{olefins (wt. \%)}}$$

$$C3 \text{ selectivity (wt. \%)} = \frac{GC\ C3\ (\text{wt. \%})}{\sum GC\ C3, 5, 6, 7, 8\ \text{olefins (wt. \%)}}$$

$$C4 \text{ conversion (wt. or mol \%)} = 1 - \frac{GC\ C4\ (\text{wt. \%})}{C4\ \text{feed (wt. \%)}}$$

Example 2: Catalyst Composition on Disproportionation Activity

Figure 3:
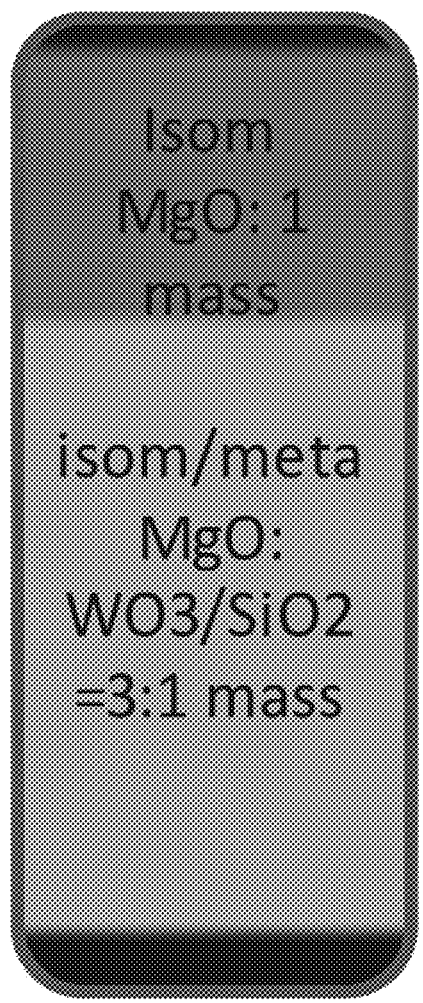
FIG. 3 shows a non-limiting example of catalyst incumbent loading configuration in a reactor for on-purpose production of propylene from ethylene and butenes.

Different catalyst loadings were investigated. In some embodiments a load ratio of $MgO:(MgO:WO_3/SiO_2)=1:(3:1)$ (see FIG. 3) is used for Raff2 butene feeds, which have a composition of B2/B of approximately 50%. In contrast, dimer butene feed is rich with B2, for example, in some embodiments B2/B is about 90%, including about 91%-92%. In some embodiments, MgO is sufficiently active at low temperatures to permit reduction in MgO usage, while still maintaining desirable butene isomerization activity. The following table provides butene compositions in dimer and Raff2 feeds in some embodiments.

| Butene source | Dimer | Raff2 |
| --- | --- | --- |
| Butene-1 (wt. %) | 9 | 25 |
| Butene 2 (wt. %) | 91 | 23 |
| Others (wt. %) | 0 | saturates |
| B2/B (wt. %) | 91 | 52 |

The effects of temperature on catalyst were evaluated and an optimized catalyst loading configuration for both dimer and Raff2 were identified. Raff2 or Raffinate 2 refers to C4 product streams after steam cracking and removals of butadiene and isobutylene. Dimer butene refers to C4 product made from selective ethylene dimerization using nickel based homogeneous catalysts. The results showed that reducing the process temperature from 350° C. to 275° C. was beneficial in some embodiments for both B1 and B2 feeds to achieve a higher C3 selectivity and slower catalyst decay. Similar effects have also been observed at plant implementation when 530° F. (277° C.) was used. A longer catalyst on-stream-time, i.e. 50% extended lifetime was achieved, in some embodiments.

By partially replacing MgO in incumbent catalyst load with $WO_3/SiO_2$, alternative catalyst configurations such as a $MgO:WO_3/SiO_2$ blend weight ratio of 3:1 to 1:4 may be used for propylene production in some embodiments. In some embodiments, the reactor may be loaded with a 3:1 ratio of $MgO:WO_3/SiO_2$ blend without topping it with one part of MgO layer without affecting reactor performance. In other embodiments, $WO_3/SiO_2$ was exclusively used for propylene production from ethylene and butene feeds.

Studies were carried out to optimize the reactor catalyst loading. In some embodiments, the catalyst composition was optimized to work with different butene streams which contain different ratios of B1 and B2. These studies first utilized pure B2 feed and various catalyst loads which eliminated the top MgO and reduced the MgO in the blend. The reactor catalyst volume was held constant (about 13.2 mL). For a pure B2 feed (Table 1), replacing the top MgO layer alone had little impact on C3 production. With a pure B2 feed, when $WO_3/SiO_2$ load increased significantly (e.g. $MgO:WO_3/SiO_2$ blend weight ratio 1:4), a noticeable improvement in C3 yield was seen. The exclusively $WO_3/SiO_2$ load exhibited the highest activity, contrary to previous literature reports that MgO was needed as a promoter for propylene production using $WO_3/SiO_2$ catalysts. See, for example, U.S. Pat. Nos. 3,660,507, 3,996,166, and 4,575,575, which are incorporated herein by reference. The higher C3 selectivity and lower butene conversion of exclusively $WO_3/SiO_2$ load was attributed to less B1 participated side reactions. The reactor effluent B2/B composition ("B" is total butene) of about 96% from the pure B2 feed suggested that $WO_3/SiO_2$ may also catalyzes some butene isomerization to a small extent.

TABLE 1

The Effect of Catalyst Load on C3 Production.

| Exp. | top (MgO) | bottom mix (MgO:WO3/SiO2) | B2/B (%) | B conv (%) | C3 sel. (wt %) | C3 yield (wt %) | cat. Load (g) |
| --- | --- | --- | --- | --- | --- | --- | --- |
| 1 | 1 | 3:1 | 81.02 | 61.33 | 92.54 | 53.48 | 10.5 |
| 2 | 0 | 1:1 | 82.11 | 59.43 | 92.33 | 53.38 | 8.2 |
| 3 | 0 | 1:2 | 81.77 | 59.91 | 92.71 | 53.66 | 7.3 |
| 4 | 0 | 1:4 | 83.90 | 58.96 | 93.81 | 54.27 | 6.7 |
| 5 | 0 | WO3/SiO2 only | 95.71 | 56.03 | 98.15 | 56.52 | 6.0 |

Blended B1/B2 mixtures were purchased from Praxair and used to simulate a dimer and Raff 2 butene feeds (Table 2). With the dimer butene feed (B2/B of 91%), various catalyst loads performed similarly. There was a slightly increase of C3 yield with exclusively $WO_3/SiO_2$. The butene conversion decreased as more $WO_3/SiO_2$ was loaded as less B1 was isomerized from B2 to take place in side reactions. At 285° C., the B2/B feed composition of 91% was above the B2/B composition at isomerization equilibrium which is about 81%.

TABLE 2

Results of Various Catalyst Loads with Dimer or Raff 2 Butene Feed.

| Exp. | top (MgO) | bottom mix (MgO:WO3/SiO2) | B feed type | B2/B (%) | B conv (%) | C3 sel. (wt %) | C3 yield (wt %) |
| --- | --- | --- | --- | --- | --- | --- | --- |
| 1 | 1 | 3:1 | Dimer | 83.01 | 60.60 | 93.26 | 53.63 |
| 2 | 0 | 1:1 | Dimer | 82.97 | 60.29 | 93.26 | 53.64 |
| 3 | 0 | 1:4 | Dimer | 82.86 | 59.62 | 93.45 | 53.75 |
| 4 | 0 | WO3/SiO2 only | Dimer | 85.20 | 58.81 | 94.79 | 54.29 |
| 5 | 1 | 3:1 | Raff2 | 83.99 | 59.47 | 92.98 | 53.34 |
| 6 | 0 | 1:1 | Raff2 | 82.39 | 61.01 | 92.92 | 53.48 |
| 7 | 0 | 1:4 | Raff2 | 74.46 | 60.69 | 88.72 | 49.54 |

When a Raff2-type feed was used, the insufficient amount of MgO in Table 2 Experiment (Exp.) 7 ($MgO:WO_3/SiO_2$ blend weight ratio 1:4) led to a loss of C3 selectivity, subsequently C3 yield due to B1 involved side reactions. The 1:1 blend (Exp. 6) provided similar results as the comparison catalyst composition of exp. 5. Another advantage of increasing $WO_3/SiO_2$ while decreasing MgO loading is the reduced total catalyst mass charged inside the reactor due to the density difference between the two catalysts, e.g. $MgO\sim62$ lb/ft$^3$ and $WO_3/SiO_2\sim28$ lb/ft$^3$ even though the total catalyst load volume stays the same. Such reduced catalyst mass can alleviate fine issues generated by heavy catalyst crushing light one in additional to overall reduced catalyst cost.

Example 3: Effect of Temperature on Isomerization Activity

Figure 4:
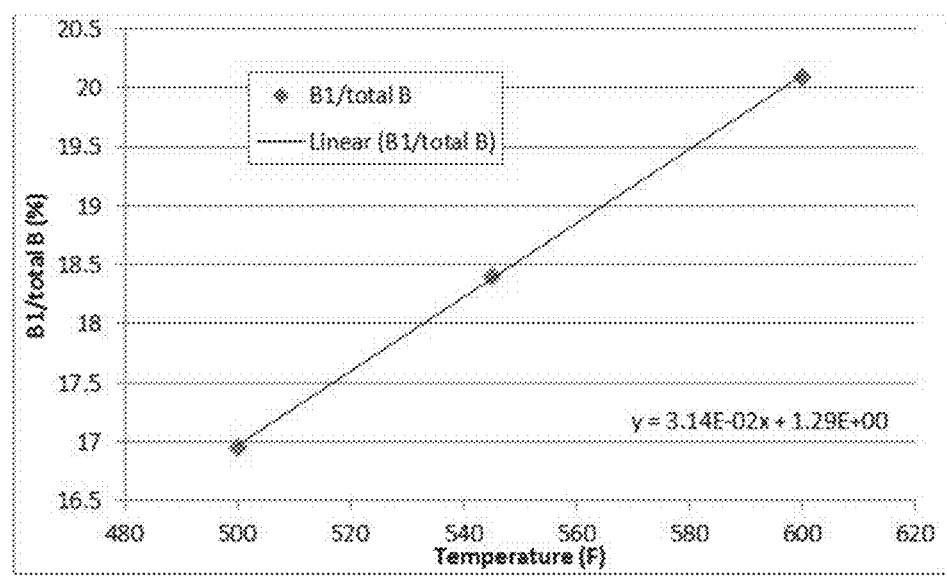
FIG. 4 shows some temperature effects on a butene isomerization equilibrium.
Figure 5:
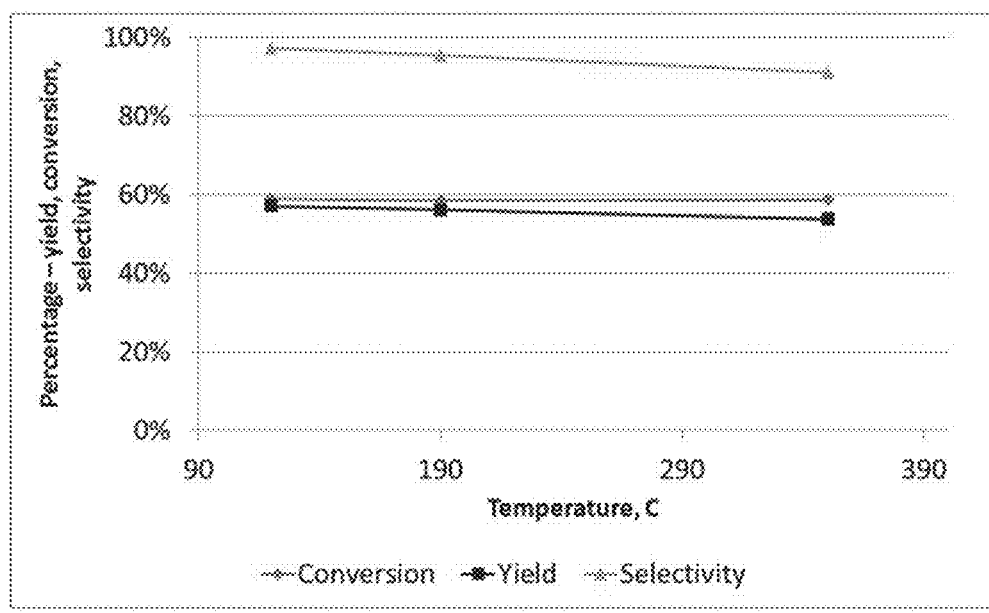
FIG. 5 shows some temperature effects on three parameters of propylene production ($C_2^=:C_4^=$=1:1 molar ratio).

In some embodiments, sufficient B1 to 2-butene (B2) isomerization (B2/B of 88% with B1 feed) can be achieved at low temperatures, i.e. 120° C. (248° F.). Despite that the catalyst performance is somewhat below equilibrium at 120° C. (e.g. B2/B is about 91% at equilibrium), a lower process temperature significantly slows down the catalyst decay (FIG. 6), reduces reactor pressure rise caused by coking, prolongs the catalyst operation time per cycle and eventually extend the catalyst overall service life due to less frequent regeneration. As also seen in FIGS. 4 and 5, B2 and propylene selectivities were found to be favored at lower process temperature.

B. Lab Scale

Figure 7:
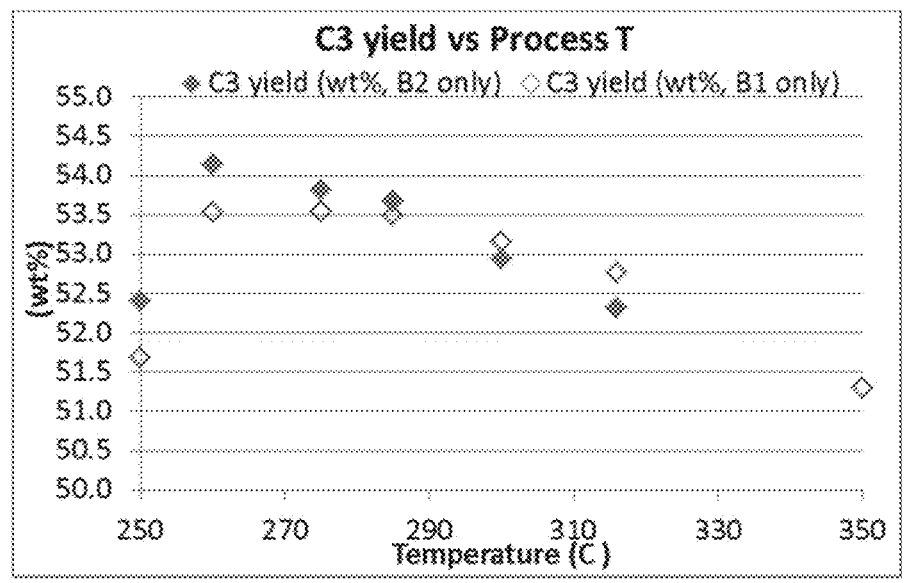
FIG. 7 shows the effect of temperature on $C_3$ yield based on two butene feedstocks, B1 and B2, where "B1" refers to 1-butene and "B2" refers to 2-butene. Each point is an average value resulting from over 40 hours of sampling. The effect of temperature on propylene yield with incumbent catalyst load was studied with neat B1 and B2 feeds.

The effect of temperature on propylene yield with reference catalyst load was studied with neat B1 and B2 feeds. For both feeds, decreasing the process temperature from 350° C. (662° F.) improved C3 yields until a plateau for B1 (260-285° C.) and a peak for B2 (260° C.) reached (FIG. 7). Below 260° C. (500° F.), the C3 yield precipitated dramatically due to significantly reduced $WO_3/SiO_2$ activity. An increase of about 0.8 wt. % and 1.8 wt. % in propylene yield was obtained for B1 and B2 feeds, respectively, at a reduced temperature. At high temperature above 285° C., the C3 yield curves from B1 and B2 were found to cross with more C3 yielded from B1 feed participated reactions.

Figure 8:
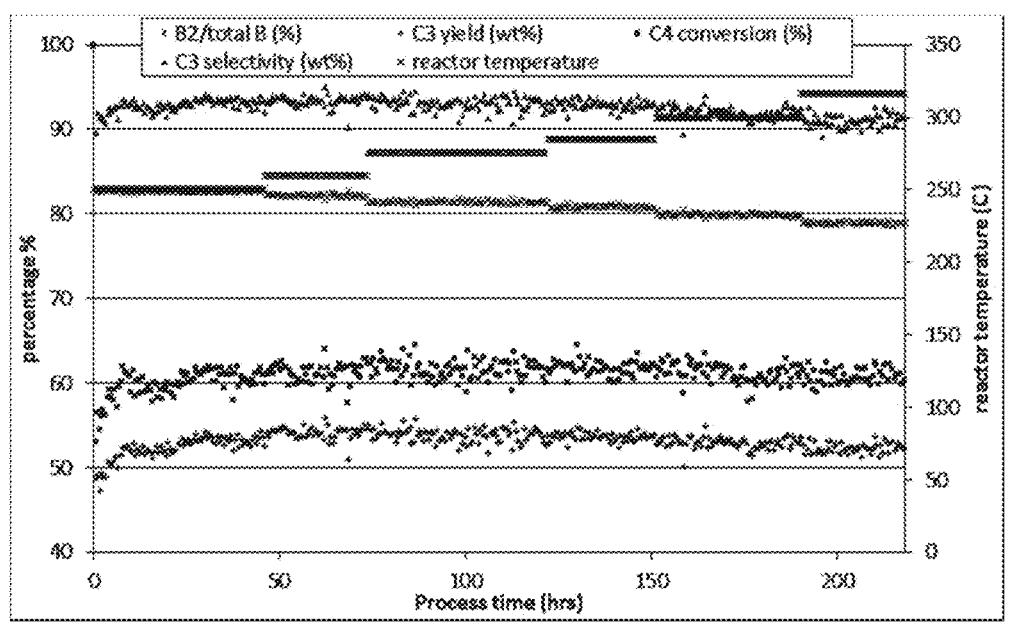
FIG. 8 shows the effect of temperature on a lab scale reaction with B2 feed, where B2 refers to 2-butene.

Detailed analysis per feed is shown for B2 in Table 3. The increased C3 yield originated mostly from improved C3 selectivity at lower temperatures, from 91 to 93%. Further temperature decrease, however, (such as 250° C.) resulted in a significant reduction in the disproportionation catalyst ($WO_3/SiO_2$) activity. The butene conversion was about 61% and was less affected by the temperature. Without being bound by any theory, it is believed that the consistent difference of B2/B between reactor effluent and the isomerization equilibrium ($\Delta$B2/B) suggests a more active metathesis than isomerization catalyst. Furthermore, the catalyst performance was found to be stable throughout the run (FIG. 8).

TABLE 3

Effect of temperature with B2 feed.
Exp. 534

| T (° C.) | B2/B eff. (%) | B conv (%) | C3 sel. (wt %) | C3 yield (wt %) |
|---|---|---|---|---|
| 250 | 82.68 | 59.94 | 92.88 | 52.40 |
| 260 | 82.15 | 61.18 | 93.41 | 54.13 |
| 275 | 81.38 | 61.58 | 93.06 | 53.82 |
| 285 | 80.80 | 61.75 | 92.94 | 53.68 |
| 300 | 79.89 | 61.13 | 92.02 | 52.93 |
| 316 | 78.92 | 60.82 | 91.08 | 52.30 |

C2 feed: 15.9 SLPH and B2 feed: 33 gram/h.
B2/B eff. was the reactor effluent analysis.

Figure 6:
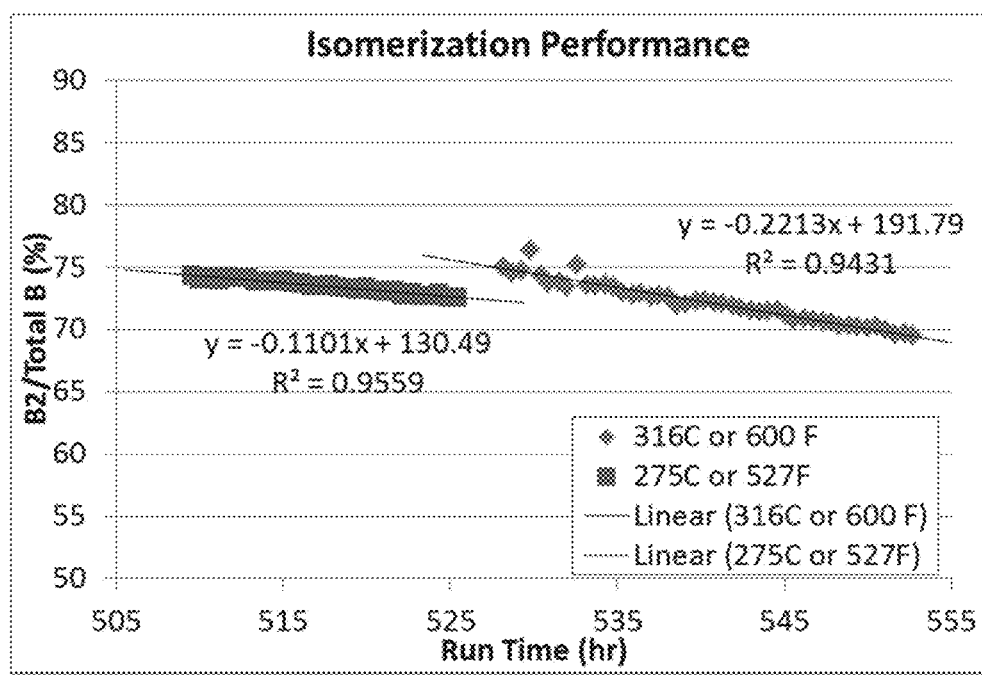
FIG. 6 shows MgO isomerization performance at temperatures of 275° C. and 316° C.

In some embodiments, increasing the temperature reduced C3 selectivity from the B1 feed, while at temperatures below 260° C., the metathesis activity was compromised. The catalyst was found to remain robust and able to regain normal activity once the temperature rose above 250° C. from 200° C. Butene conversion was found to be slightly higher for B1 feed than B2 because more B1 participated in side reactions due to slower isomerization, which was also supported by higher B2/B composition differences ($\Delta$B2/B) between reactor effluent and equilibrium. The isomerization efficiency was found to improve upon raising temperatures. Comparing the $\Delta$B2/B of the experiments from both the B1 and the B2 feeds indicated that MgO isomerization improved at a faster rate than the disproportionation catalyst ($WO_3/SiO_2$) when the temperature process temperature was raised above 250° C. but when the temperature was increased above about 300° C., the activity of the MgO catalyst decayed also quickly (FIG. 6).

C. Reactor Scale

The different temperatures were explored on a plant scale reactor with dimer butene feed having higher B2 than equilibrium (vide infra). Reducing temperatures led to slight improvement in C3 selectivities, but the effluent B2/B content and butene conversions under constant butene feeds were increased. The higher B2/B composition in the reactor effluent was consistent with suppressed isomerization activity, thereby minimizing B1 involved side reactions. Due to increased butene conversion, additional fresh butene was fed to the reactor to maintain the production rate as the unreacted butene was recycled. With trace ethylene coming along with fresh butene from ethylene dimerization reaction, the ethylene and butene feed ratio to the disproportionation reactor was slightly increased, contributing to the higher butene conversion. Overall, at least 2 wt. % of additional C3 was produced as a result of decreasing the process temperature from 600° F. to 525° F.

Same benefit of reducing process temperature on propylene yield improvement was also observed with Raff2 butene feed (vide supra). Despite of slightly reduced initial butene isomerization below equilibrium, a desirable compromise between catalyst activity and decay was reached in addition to improved butene conversion. The catalyst run time per regeneration recycle was extended 33+% longer gauged by the reactor pressure drop.

Example 4: Effect of Ethylene to Butene Ratio on Activity

Figure 9:
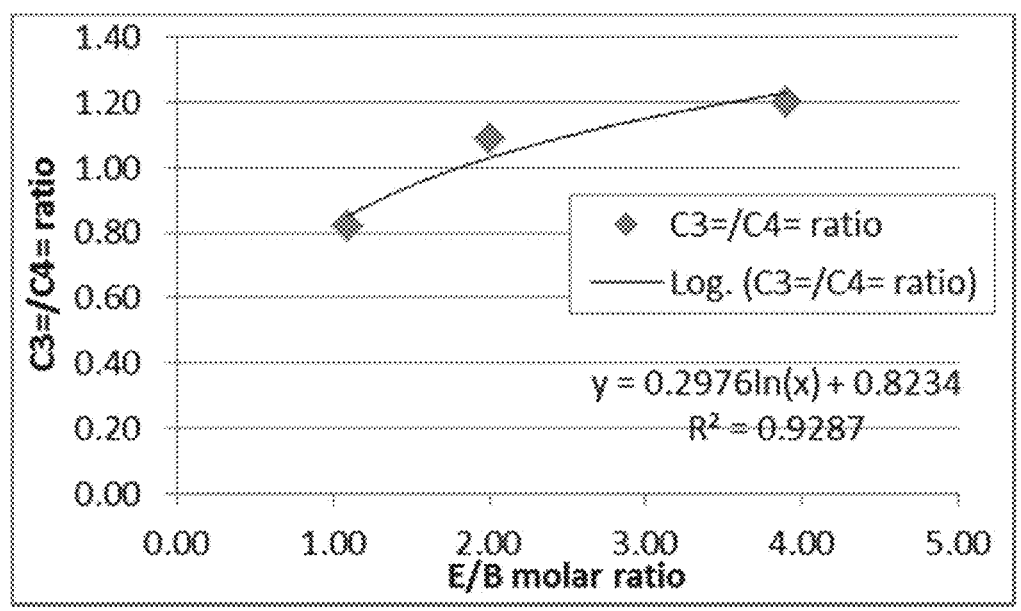
FIG. 9 shows some effects of an ethylene/butene ratio on C3 production.

The effect of the ethylene/butene (E/B) ratio with B2 feed was investigated. Increasing the E/B molar ratio from 1.1:1 to 2.0:1 and 3.9:1 enhanced the B conversion and C3 selectivity. The C3 yield was lower for the 3.9:1 ratio due to effluent diluted by excess of unreacted ethylene. In plant process, the unreacted feeds are recycled and consequently the C3 production rate is ultimately improved at higher EB ratio as evidenced by C3=/C4=ratio (Table 4). However, the increase in C3 production rate was not observed to be linear (FIG. 9). Without butene, the catalyst still produced a small amount of propylene from ethylene. Without being bound by any theory, it is believed that this propylene production is due to some in situ ethylene dimerization taken place by $WO_3/SiO_2$ catalyst.

TABLE 4

Effect of E/B ratio on propylene production.
Exp. 564 C2:B2 = varied

| T (° C.) | C2/B2 | B2/B (%) | B conv (%) | C3 sel. (wt %) | C3 yield (wt %) | C3=/C4= ratio |
|---|---|---|---|---|---|---|
| 285 | 1.1 | 79.97 | 58.25 | 90.95 | 52.30 | 0.82 |
| 285 | 2.0 | 81.21 | 64.75 | 96.30 | 54.91 | 1.09 |
| 285 | 3.9 | 81.19 | 70.64 | 98.66 | 51.52 | 1.20 |
| 285 | C2only | 32.83 | NA | 98.43 | 0.12 | NA |

Table 4: C2/B2 is the molar ratio of ethylene and butene. B2/B is the effluent butene analysis.

All of the compounds, complexes, and methods disclosed and claimed herein can be made and executed without undue experimentation in light of the present disclosure. While the compounds, complexes, and methods of this disclosure have been described in terms of certain embodiments, it will be apparent to those of skill in the art that variations may be applied to the compounds, complexes, and methods, as well as in the steps or in the sequence of steps of the method described herein without departing from the concept, spirit, and scope of the appended claims. More specifically, it will be apparent that certain compounds which are chemically related may be substituted for the compounds described herein while the same or similar results would be achieved. Similar substitutes and modifications apparent to those skilled in the art are deemed to be within the spirit, scope and concept of the present disclosure as defined by the appended claims.

REFERENCES

The following references to the extent that they provide exemplary procedural or other details supplementary to those set forth herein, are specifically incorporated herein by reference.

U.S. Pat. No. 3,660,507
U.S. Pat. No. 3,996,166
U.S. Pat. No. 4,575,575
U.S. Pat. No. 6,683,019
U.S. Pat. No. 8,586,813

What is claimed is:

1. A method for producing propylene comprising:
   (a) obtaining a catalyst composition comprising an isomerization catalyst comprising MgO and a disproportionation catalyst comprising a transition metal oxide deposited on a solid support, wherein the weight ratio of the isomerization catalyst to the disproportionation catalyst is from 10:1 to 1:10; and
   (b) reacting butene with ethylene at a temperature from about 500° F. (260° C.) to about 650° F. (350° C.) in the presence of the catalyst composition under conditions sufficient to produce propylene;
   wherein the temperature is optionally decreased for increasing propylene production and reducing catalyst compositional decay.

2. The method of claim 1, wherein the ethylene and the butene are reacted at a temperature from about 500° F. (260° C.) to about 550° F. (288° C.).

3. The method of claim 1, wherein the weight ratio of the isomerization catalyst to the disproportionation catalyst is from about 4:1 to about 1:4.

4. The method of claim 1, wherein the weight ratio of the isomerization catalyst to the disproportionation catalyst is about 1:1.

5. The method of claim 1, wherein the isomerization catalyst is a zeolite, alumina, or a basic metal oxide selected from the group consisting of an alkali metal oxide, an alkaline earth metal oxide and a rare earth metal oxide.

6. The method of claim 1, wherein the transition metal oxide is an oxide of molybdenum, tungsten, cobalt, ruthenium, rhenium or a mixture thereof.

7. The method of claim 6, wherein the transition metal oxide is $WO_3$.

8. The method of claim 1, wherein the solid support is silica.

9. The method of claim 1, wherein the ethylene and the butene are reacted at a pressure from about 5 psig (0.14 MPa) to about 600 psig (4.24 MPa).

10. The method of claim 1, wherein the mole ratio of ethylene to butene is from about 0.5:1 to about 5:1.

11. The method of claim 1, wherein the weight hourly space velocity of the reaction is from about 1 $hr^{-1}$ to 100 $hr^{-1}$.

12. The method of claim 1, wherein the method results in:
   (a) a butene conversion percentage of greater than 55% relative to the amount of butene;
   (b) a propylene selectivity percentage of greater than 85% relative to the total reaction products; or
   (c) a propylene yield of greater than 50% based on the amount of butene.

* * * * *

UNITED STATES PATENT AND TRADEMARK OFFICE
CERTIFICATE OF CORRECTION

PATENT NO. : 10,029,960 B2
APPLICATION NO. : 15/414384
DATED : July 24, 2018
INVENTOR(S) : Zhang et al.

Page 1 of 1

It is certified that error appears in the above-identified patent and that said Letters Patent is hereby corrected as shown below:

In the Specification

In Column 2, Line 66, after "aspects," insert -- all --
In Column 10, Line 61, delete "additional" and insert -- addition --

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*